United States Patent [19]

Otoi et al.

[11] 4,233,212
[45] Nov. 11, 1980

[54] PROCESS FOR PRODUCING A FINE POWDER OF SILK FIBROIN

[75] Inventors: Kiyoshi Otoi, Maruko; Yukio Horikawa, Matsubara, both of Japan

[73] Assignees: Kanebo, Ltd., Tokyo; Kanebo Spun Silk, Ltd., Nagano, both of Japan

[21] Appl. No.: 79,864

[22] Filed: Sep. 28, 1979

[30] Foreign Application Priority Data

Apr. 17, 1979 [JP] Japan ................................ 54-47382

[51] Int. Cl.$^3$ ............................................. C07G 7/00
[52] U.S. Cl. .................................. 260/123.7; 424/63; 424/69
[58] Field of Search ..................................... 260/123.7

[56] References Cited

U.S. PATENT DOCUMENTS

| | | | |
|---|---|---|---|
| 1,714,039 | 5/1929 | Muto et al. | 260/123.7 X |
| 2,145,855 | 2/1939 | Bley | 260/123.7 UX |
| 2,260,276 | 10/1941 | Lawson et al. | 260/123.7 X |

FOREIGN PATENT DOCUMENTS

519544 3/1940 United Kingdom .................. 260/123.7

OTHER PUBLICATIONS

Chem. Abstracts, vol. 47, 1953, 2942g-h, Nomura et al.
Chem. Abstracts, vol. 60, 1964, 14822g-h, Akyu et al.

*Primary Examiner*—Howard E. Schain
*Attorney, Agent, or Firm*—Blanchard, Flynn, Thiel, Boutell & Tanis

[57] ABSTRACT

A process for producing a fine powder of high-purity silk fibroin in nonfibrous and particulate form is disclosed. The process comprises dissolving a degummed silk material in at least one solvent selected from the group consisting of an aqueous cupri-ethylenediamine solution, an aqueous ammoniacal solution of cupric hydroxide, an aqueous alkaline solution of cupric hydroxide and glycerol, an aqueous lithium bromide solution, an aqueous solution of the chloride, nitrate or thiocyanate of calcium, magnesium or zinc, and an aqueous sodium thiocyanate solution; adding a coagulating salt to the resulting aqueous silk fibroin solution having a silk fibroin concentration of from 3 to 20% by weight to coagulate and precipitate the silk fibroin; dehydrating and drying the gel so formed; and then pulverizing the resulting powder. Alternatively, the process comprises dissolving a degummed silk material in a solvent as defined above; dialyzing the resulting aqueous silk fibroin solution; subjecting the dialyzed aqueous silk fibroin solution having a silk fibroin concentration of from 3 to 20% weight to at least one treatment for coagulating and precipitating the silk fibroin, the treatment being selected from the group consisting of the addition of a coagulating salt, aeration, coagulation at the isoelectric point, exposure to ultrasonic waves, and agitation at high shear rate; dehydrating and drying the gel so formed; and then pulverizing the resulting powder. The fine powder of silk fibroin thus obtained is particularly useful as an additive for cosmetic preparations.

11 Claims, No Drawings

PROCESS FOR PRODUCING A FINE POWDER OF SILK FIBROIN

BACKGROUND OF THE INVENTION

This invention relates to a process for producing a fine powder of high-purity silk fibroin.

Powdered silk fibroin has heretofore been used mainly as an additive or base material for make-up cosmetics, because of its characteristic features such as moderate moisture absorption and retention properties, high affinity for the skin, excellent slip properties on the skin, good hydrophilic-lipophilic balance, and adequate ultraviolet absorption properties.

Currently available silk fibroin powders include, for example, (1) a powder of silk fibroin in fibrous form which is produced, as described in Japanese Patent Publication No. 24920/'75, by reducing silk thread directly to powder or by subjecting silk thread to a chemical treatment for its embrittlement and then reducing it to powder and (2) a powder of silk fibroin in granular form which is produced, as described in Japanese Patent Publication No. 4947/'51, by dissolving silk fibroin in a concentrated solution of a suitable neutral salt, dialyzing the resulting solution, spray-drying the colloidal solution so formed, and then grinding the resulting gel of silk fibroin.

The former powder of silk fibroin in fibrous form consists of filamentous fibers cut in short lengths rather than nearly globular particles, and the silk fibroin molecules contained therein are oriented in the direction of the fiber axis. Accordingly, when used as a base material for make-up cosmetics, this powder gives rise to various difficulties. For example, in mixing this powder with other ingredients in globular form, it is so liable to aggregation that a homogeneous final product is hardly obtained. Even if such a product is obtained, it shows poor slip properties upon application to the human skin and may occasionally produce round agglomerates of silk fibroin. Moreover, when used as an additive for cosmetic preparations, this powder has poor compatibility with other ingredients because of its high degree of molecular orientation, and has an inadequate moisture-controlling effect on the skin because of its poor ability to be swollen by water. Thus, it can be said that these difficulties prevent us from making good use of the excellent properties of silk fibroin.

Also in Japanese Patent Publication No. 1941/'64 is disclosed a process for producing silk fibroin suitable for use in chromatography. This process comprises dissolving silk fibroin in a cuprammonium solution or a solution of a copper complex (for example, a cupriethylenediamine solution), neutralizing the resulting solution with an acid, and then adding an alcohol to the neutralized solution to form a white precipitate of silk fibroin. As a result of confirmatory tests made by the present inventors, it has been found that this process requires a very large amount of alcohol and, moreover, the resulting precipitate is too sticky to be separated by filtration. Furthermore, the fine powder of silk fibroin produced by this process has such an abnormal degree of hydrophilic nature as to be soluble in hot water in an extreme case, and cannot be used as an additive for cosmetic preparations because of its adherance to the skin. Similarly, the aforesaid powder of silk fibroin produced by dissolving silk fibroin in a concentrated solution of a suitable neutral salt, dialyzing the resulting solution, and spray-drying the colloidal solution so formed is also abnormally hydrophilic and, therefore, unsuitable for use as an additive for cosmetic preparations.

In addition, there have been proposed other processes which involves hydrolyzing silk thread with an acid of alkali to prepare a silk fibroin solution and then precipitating the silk fibroin either by neutralization or by the addition of an alcohol. In the fine powders of silk fibroin produced by these processes, however, the molecular weight is reduced to those of oligomers and the characteristic properties of silk are completely lost.

X-ray diffraction analysis and infrared spectroscopic analysis have revealed that, in the conventional fine powders of silk fibroin produced by various processes involving the dissolution of silk fibroin, the silk fibroin molecules contained therein have either a random configuration or the α-configuration and the degree of crystallinity is so low as to imply the amorphous state rather than the crystalline state.

In order to overcome the above-described difficulties, the present inventors have made a series of intensive and extensive studies on the principle of rendering finely powdered silk fibroin hydrophobic to such a degree that it shows no stickiness in the presence of water, and have thereby completed this invention.

BRIEF SUMMARY OF THE INVENTION

It is an object of this invention to provide a fine powder of silk fibroin in nonfibrous and particulate form. Another object of this invention is to provide a fine powder of silk fibroin in nonfibrous and particulate form which, when used as an additive for cosmetic preparations, exhibits good compatibility and dispersibility with other base materials, moderate swelling properties, and excellent slip properties without adherance to the skin. Still another object of this invention is to provide a process for producing a fine powder of silk fibroin in nonfibrous and particulate form which permits its industrial production with great ease and at low cost.

In accordance with one embodiment of this invention, there is provided a process for producing a fine powder of silk fibroin in nonfibrous and particulate form which comprises the steps of dissolving a degummed silk material in at least one solvent selected from the group consisting of an aqueous cupriethylenediamine solution, an aqueous ammoniacal solution of cupric hydroxide, an aqueous alkaline solution of cupric hydroxide and glycerol, an aqueous lithium bromide solution, an aqueous solution of the chloride, nitrate or thiocyanate of calcium, magnesium or zinc, and an aqueous sodium thiocyanate solution; adding a coagulating salt to the resulting aqueous silk fibroin solution having a silk fibroin concentration of 3 to 20% by weight to coagulate and precipitate the silk fibroin; dehydrating and drying the gel so formed; and then pulverizing the resulting powder.

In accordance with another embodiment of this invention, there is also provided a process for producing a fine powder of silk fibroin in nonfibrous and particulate form which comprises the steps of dissolving a degummed silk material in at least one solvent selected from the group consisting of an aqueous cupriethylenediamine solution, an aqueous ammoniacal solution of cupric hydroxide, an aqueous alkaline solution of cupric hydroxide and glycerol, an aqueous lithium bromide solution, an aqueous solution of the chloride, nitrate or thiocyanate of calcium, magnesium or zinc, and an aqueous sodium thiocyanate solution; dialyzing the resulting aqueous silk fibroin solution; subjecting the dialyzed aqueous silk fibroin solution having a silk fibroin concentration of from 3 to 20% by weight to at least one treatment for coagulating and precipitating the silk fibroin, the treatment being selected from the group consisting of the addition of a coagulating salt, aeration, coagulation at the isoelectric point, exposure to ultrasonic waves, and agitation at high shear rate; dehydrating and drying the gel so formed; and then pulverizing the resulting powder.

The fine powder of silk fibroin in nonfibrous and particulate form which is produced by the process of this invention has an average molecular weight of not less than 50,000, a degree of molecular orientation equal to not greater than one-half that of natural silk thread, particle diameters of from 1 to 100μ, and a bulk density of from 0.1 to 0.7 g/cm$^3$, and contains at least 50% by weight of hot-water-insoluble fibroin having the β-configuration.

DETAILED DESCRIPTION OF THE PREFERRED EMBODIMENTS

The solvent for silk fibroin which is used in the process of this invention can be an aqueous cupriethylenediamine solution, an aqueous ammoniacal solution of cupric hydroxide (Schweitzer's reagent), an aqueous alkaline solution of cupric hydroxide and glycerol (Roe's reagent), an aqueous lithium bromide solution, an aqueous solution of the chloride, nitrate or thiocyanate of calcium, magnesium or zinc, and an aqueous sodium thiocyanate solution. However, it is preferable to use an aqueous solution of the chloride or nitrate of calcium or magnesium, because of its low cost and convenience for use. The concentrations of these aqueous solutions may vary according to the type of solute used, temperature, and the like. Where an aqueous solution of a metal salt is used, its concentration is generally from 5 to 80% by weight, preferably from 20 to 70% by weight, and most preferably from 25 to 60% by weight.

The silk material which is used in the process of this invention can be cocoons, raw silk, waste cocoons, raw silk waste, bisu (unreelable cocoons), silk fabric waste, bourette, and the like. Prior to use, the silk material is degummed or freed from sericin by any conventional procedure. For example, it is washed in warm water containing a surface-active agent or an enzyme according to the need, and then dried.

Using a suitable apparatus such as kneader, the degummed silk material is dissolved in the solvent which is selected from among the aforesaid aqueous solutions and preheated to a temperature of from 60° to 95° C. and preferably from 70° to 85° C. The solvent is generally used in an amount of from 2 to 50 parts by weight and preferably from 3 to 30 parts by weight per parts by weight of the degummed silk material.

Where the coagulation step is carried out by the addition of a coagulating salt, the resulting aqueous silk fibroin solution may be used directly. However, the aqueous silk fibroin solution must be dialyzed before it can be subjected to any one of the other treatments. It is also preferable to dialyze the aqueous silk fibroin solution in case of the addition of a coagulating salt.

In the dialysis step, the salt contained in the aqueous silk fibroin solution is almost completely removed by means of a dialyzer using semipermeable membranes or hollow fibers, typically made of cellophane. In order that a gel of silk fibroin may be formed stably and rapidly, there must be a proper correlation between the volume of the solution to be dialyzed and the surface area of the dialysis membrane. More specifically, desalting should be carried out by the use of a multilayer membrane structure or bundled hollow-fiber structure satisfying the condition expressed by $$\frac{\text{Membrane Surface Area (cm}^2\text{)}}{\text{Priming Volume (cm}^3\text{)}} \geq 10$$

where the priming volume means the internal volume within the tubing or between the layers. If the value of the above-defined ratio is less than 10, the removal of the salt through the membrane is not effected rapidly and, moreover, not a stable gel of silk fibroin but only a sticky precipitate is formed in the succeeding coagulation step. In order to carry out the process of this invention smoothly and economically, the above-defined ratio should preferably have a value of not less than 30 and most preferably a value of not less than 50. In the case of a multilayer membrane structure, for example, it is necessary to keep the spacing between layers at 2 mm or less for the purpose of satisfying the aforesaid condition. In the case of a bundled hollow-fiber structure which is more suited to the satisfaction of the aforesaid condition, it is necessary to use hollow fibers having a diameter of 4 mm or less.

In the process of this invention, the dialyzed aqueous silk fibroin solution has a very low residual salt concentration of from 0.003 to 0.06% by weight, so that an extremely high purity of silk fibroin can be achieved.

Before being transferred to the coagulating step, the aqueous silk fibroin solution is adjusted to a silk fibroin concentration of from 3 to 20% by weight, preferably from 4 to 15% by weight, and most preferably from 5 to 10% by weight. Where the dialysis step is omitted, the aqueous silk fibroin solution is necessarily prepared so that it will have a silk fibroin concentration of from 3 to 20% by weight. Where the aqueous ailk fibroin solution is subjected to dialysis, however, the dialyzed aqueous silk fibroin solution may be either concentrated or diluted until the desired silk fibroin concentration is attained. If the silk fibroin concentration is less than 3% by weight, a homogeneous mass of gel is not formed and a long time is required for the coagulation step (which leads to an economic loss), while if it is greater than 20% by weight, a stable mass of gel is formed but its dehydration becomes very difficult.

After adjustment of the silk fibroin concentration, the aqueous silk fibroin solution is subjected to the coagulation step. Where the addition of a coagulating salt is used, a concentrated aqueous solution of a salt such as sodium chloride, potassium chloride, sodium sulfate, potassium sulfate, ammonium sulfate, sodium nitrate, potassium nitrate, etc. is added to and mixed with the aqueous silk fibroin solution and the resulting mixture is stirred to precipitate the silk fibroin. (If a calcium salt is used in the dissolution step and a sulfate in the coagulation step, a coprecipitation of calcium sulfate takes place.) The concentration of the concentrated aqueous solution of a coagulating salt is usually adjusted so that the resulting mixture will contain from 5 to 10% by weight of the coagulating salt.

Aeration is carried out by bubbling air through the aqueous silk fibroin solution according to any suitable technique. For each liter of the aqueous silk fibroin solution, air is usually fed at a rate of at least 0.1 l min. The aeration time is generally 10 minutes or more, though it depends on the feed rate of air.

Coagulation at the isoelectric point is carried out by adding an inorganic acid (such as hydrochloric acid, sulfuric acid, etc.) or an organic acid (such as acetic acid, citric acid, etc.), with stirring, to the aqueous silk fibroin solution until its pH reaches 4.5. Then, this aqueous silk fibroin solution is generally allowed to stand at room temperature for a period of 10 minutes or more.

Exposure to ultrasonic waves is carried out by placing the aqueous silk fibroin solution in an ultrasonic wave generator and exposing it, with stirring, to ultrasonic waves which generally have frequencies of 30 kHz or higher. The silk fibroin is coagulated by continuing this treatment at room temperature for a period of 1 hour or more.

The silk fibroin can also be precipitated simply by agitating the aqueous silk fibroin solution. However, this agitation must be carried out at a high shear rate which is generally 50/sec or more and preferably 100/sec or more. The agitation time required for gelation is generally 1 hour or more, though it depends on the concentration of the aqueous silk fibroin solution, the shear rate, and the like.

During this agitation, methyl alcohol, ethyl alcohol, isopropyl alcohol, or acetone may be added to the aqueous silk fibroin solution so that the rate of $\beta$-configuration can be raised to the order of 70%. The amount of alcohol or acetone added is suitably from 1 to 100% by weight based on the weight of the aqueous silk fibroin solution.

The mass of gel so formed is subjected to the dehydration step. This step is preferably carried out by the use of a centrifuge, and the stable mass of gel formed in accordance with this invention is generally dehydrated to a water content of the order of from 100 to 500% by weight based on the weight of the solid contained therein. During the dehydration step carried out by centrifugation, the mass of gel is broken to fragments of small sizes which can then be easily dried to the absolute dry state. This drying step is carried out at a temperature of from 60° to 120° C. under normal or reduced pressure.

The powder of silk fibroin thus obtained is subsequently pulverized by the use of a pulverizer such as hammer mill or jet mill. The particle diameters should be adjusted to a range of from 1 to 100$\mu$, preferably from 4 to 80$\mu$, and most preferably from 5 to 30$\mu$. If the particle diameters are less than 1$\mu$, the resulting fine powder shows poor dispersibility and compatibility when used as an additive for cosmetic preparations, while if they are greater than 100$\mu$, the resulting fine powder has low affinity for the skin and poor slip properties on the skin. Since the present process for producing a fine powder of silk fibroin involves gelation followed by dehydration and drying, the resulting silk fibroin particles are considered to have very minute pores to which their good moisture absorption and retention properties are attributable. However, this may lead to the disadvantage that the fine powder of silk fibroin becomes excessively swollen in certain applications. It is desirable, therefore, to subject the resulting fine powder of silk fibroin to a wet heat treatment comprising exposure to saturated steam at a temperature of 50° C. or above and preferably from 80° to 120° C. This treatment may be applied either to the powder ensuing from the dehydration and drying step or to the fine powder ensuing from the pulverization step. Moreover, the fine powder of silk fibroin can further be insolubilized in hot water by, proir to drying, heating the dehydrated gel at a temperature of 50° C. or above in an aqueous solution of a neutral salt such as sodium chloride, potassium chloride, sodium sulfate, potassium sulfate, ammonium sulfate, sodium nitrate, etc. or in an organic solvent such as acetone, alcohol, etc.

The fine powder of silk fibroin produced in accordance with this invention has a degree of crystallinity of not less than 20%, preferably not less than 30%, and most preferably not less than 40%. The degree of crystallinity was determined in the following manner: An aqueous silk fibroin solution containing 5% by weight of a silk fibroin produced in accordance with this invention was poured on a Teflon plate and then dried at a temperature of 50° C. to form a silk fibroin film having a thickness of about 60$\mu$. This silk fibroin film was regarded as amorphous (0%) while raw silk as completely crystalline (100%). The degree of crystallinity was expressed as a relative value on the scale defined between these standard points.

The fine powder of silk fibroin produced in accordance with this invention has a bulk density of from 0.1 to 0.7 g/cm$^3$ and preferably from 0.2 to 0.6 g/cm$^3$ as measured in the dry state. If the bulk density is less than 0.1 g/cm$^3$, the fine powder of silk fibroin has poor compatibility and dispersibility and, when used as an additive for cosmetic preparations, may produce a phase separation. If it is greater than 0.7 g/cm$^3$, the fine powder of silk fibroin is decreased in moisture absorption and retention properties. The bulk density was measured in the most closely packed state by means of a commercially available powder tester (manufactured and sold by Hosokawa Tekkosho, Ltd.).

The fine powder of silk fibroin produced in accordance with this invention contains at least 50% by weight of hot-water-insoluble fibroin having the $\beta$-configuration. If the content of hot-water-insoluble fibroin is less than 50% by weight, the fine powder is extremely hydrophilic and liable to deterioration. Moreover, when used as a base material for cosmetic preparations, it shows a high degree of stickiness and gives a disagreeable feeling to the skin. The content of hot-water-insoluble fibroin (or rate of $\beta$-configuration) was determined in the following manner: 10 G. (absolute dry weight) of a fine powder of silk fibroin to be tested was boiled in 1 l of hot water at a temperature of 100° C. for a period of 15 minutes, and the undissolved fraction of silk fibroin was absolutely dried and weighed. Then, the content of hot-water-insoluble fibroin was calculated from the equation:

$$\text{Content of Hot-water-insoluble Fibroin} = \frac{W}{10} \times 100 \text{ (\% by weight)}$$

where W stands for the absolute dry weight (in g) of the undissolved fraction of silk fibroin.

The fine powder of silk fibroin produced in accordance with this invention has a high purity as well as good moisture absorption and retention properties. Accordingly, it is very useful as an additive for cosmetic and pharmaceutical preparations. It is also suitable for use as an adsorbent in pharmaceutical and hygienic applications, because the silk fibroin particles contained therein have very minute pores owing to the special manner of production.

The present invention is further illustrated by the following examples. In these examples, parts are by weight unless otherwise indicated.

EXAMPLE 1

In this example, spun silk waste was used as the starting material for the production of fine powders of silk fibroin. One hundred parts of spun silk waste was immersed in a solution of 30 parts of marseille soap in 3,000 parts of water, stirred at 95°–98° C. for 3 hours to reduce its gum content to 0.1% by weight or less, washed with water, and then dried in hot air at 80° C. Anhydrous zinc chloride ($ZnCl_2$) was dissolved in water to prepare its aqueous solutions having the respective zinc chloride concentrations indicated in Table 1, which were then heated to 70° C. By stirring in a kneader, various amounts of spun silk waste degummed as above were dissolved in 100 parts each of the zinc chloride solutions to prepare silk fibroin solutions having the respective silk fibroin concentrations indicated in Table 1. As can be seen from the data of Table 1, the process of this invention allowed the spun silk waste to be dissolved easily. However, when the zinc chloride concentration was less than 5% by weight as in Run 1-(1), it was hardly dissolved even after a long period of time (24 hours or more).

Then, each of the resulting silk fibroin solutions was mixed with a concentrated solution containing the same amount of ammonium sulfate as that of zinc chloride used, so that a gel-like precipitate of silk fibroin was formed. The precipitate was allowed to stand at 70° C. for 20 minutes in the concentrated solution of ammonium sulfate, separated by filtration, washed with water, and then dehydrated by centrifugation. As can be seen from the data of Table 1, the process of this invention caused a homogeneous mass of gel to be formed in an instant or within several hours and, when dehydrated by centrifugation, the mass of gel was broken to fragments having sized of the order of several millimeters. However, when the silk fibroin concentration was less than 3% by weight as in Runs 1-(5) and 1-(11) or when it was greater than 20% by weight as in Runs 1-(10) and 1-(16), not a homogeneous mass of gel but a white precipitate was formed. This precipitate was too sticky to be separated by conventional filtration under reduced pressure. When it was placed in a cloth bag and then centrifuged, it aggregated into a bulky and sticky mass which was very difficult of dehydration and drying. In each test run, the dehydrated gel was dried in a hot-air oven set at 90°–100° C. or a vacuum dryer set at 70° C. to obtain a fine granular product of silk fibroin suitable for direct pulverization. Subsequently, the granular product was pulverized with a jet mill to obtain a fine powder of silk fibroin consisting of nearly globular particles, 98% of more of which had diameters of 5–40μ.

When measurements of the bulk density were made, all the fine powders of silk fibroin produced in accordance with this invention, and not those produced in the control runs, were found to have values within the range of 0.1–0.7 $g/cm^3$. The reason for this seems to be that the particles had minute pores owing to the special manner of production in which a powder is derived from a homogeneous mass of gel.

When measurements were made of the content of hot-water-insoluble fibroin or rate of β-configuration, all the fine powders produced in accordance with this invention were found to have values of not less than 50% by weight. In addition, X-ray diffraction analysis revealed that the degree of crystallinity was not less than 25% in all the fine powders of silk fibroin produced in accordance with this invention.

TABLE 1

| | | Zinc Chloride Concentration (wt. %) | Silk Fibroin Concentration (wt. %) | Solubility* | Form of Gel | Rate of β-configuration (%) | Bulk Density (g/cm³) |
|---|---|---|---|---|---|---|---|
| 1-(1) | Control Run | 3 | 3 | X | — | — | — |
| 1-(2) | Test Run | 10 | 3 | O | Soft mass | 55 | 0.59 |
| 1-(3) | " | 10 | 6 | O | " | 58 | 0.65 |
| 1-(4) | " | 10 | 10 | O | " | 52 | 0.68 |
| 1-(5) | Control Run | 20 | 1 | ◎ | Sticky precipitate | 20 | — |
| 1-(6) | Test Run | 20 | 10 | ◎ | Soft mass | 63 | 0.60 |
| 1-(7) | " | 20 | 20 | O | " | 60 | 0.65 |
| 1-(8) | " | 40 | 10 | ◎ | " | 68 | 0.58 |
| 1-(9) | " | 40 | 20 | ◎ | " | 64 | 0.60 |
| 1-(10) | Control Run | 40 | 25 | Δ | Sticky precipitate | 5 | — |
| 1-(11) | " | 60 | 1 | ◎ | Sticky precipitate | 0 | — |
| 1-(12) | Test Run | 60 | 10 | ◎ | Soft mass | 68 | 0.53 |
| 1-(13) | " | 60 | 20 | ◎ | " | 63 | 0.60 |
| 1-(14) | " | 80 | 10 | ◎ | " | 56 | 0.66 |
| 1-(15) | " | 80 | 20 | ◎ | " | 51 | 0.68 |
| 1-(16) | Control Run | 80 | 25 | O | Sticky precipitate | 5 | — |
| 1-(17) | " | 90 | 10 | ◎ | Somewhat sticky precipitate | 44 | 0.85 |

*Rated as insoluble (X) when the spun silk waste was not dissolved even after 24 hours, sparingly soluble (Δ) when it was dissolved in 1–2 hours, soluble (O) when it was dissolved in 0.5–1 hour, or very soluble (◎) when it was dissolved within 0.5 hour.

EXAMPLE 2

Spun silk waste was degummed in the same manner as described in Example 1 and used as the starting material for the production of fine powders of silk fibroin. Calcium chloride ($CaCl_2.4H_2O$) was dissolved in water to prepare its aqueous solution having the respective calcium chloride concentrations indicated in Table 2, which were then heated to 95° C. By stirring in a kneader, 10 parts of spun silk waste degummed as above was dissolved in 100 parts each of the calcium chloride solutions to prepare a series of silk fibroin solutions. As can be seen from the data of Table 2, the process of this invention allowed the spun silk waste to be dissolved easily. However, when the calcium chloride concentration was less than 10% by weight as in Run 2-(1), it was hardly dissolved even after a long period of time (24 hours or more).

The resulting aqueous silk fibroin solutions were then desalted by passing each of them through a dialyzer of the hollowfiber type at a rate of 1 l/hr. This dialyzer was composed of 2,000 hollow fibers of regenerated cellulose having an internal diameter of 200μ, a membrane thickness of 20μ, and a length of 500 mm, both ends of these hollow fibers being bundled and sealed without blocking up their hollow bores. In this case, the ratio of membrane surface area (cm²) to priming volume (cm³) had a value of 100. After completion of the dialysis, the aqueous silk fibroin solutions had silk fibroin concentrations of 3.2–6.7% by weight and residual calcium chloride concentrations of 0.007–0.033% by weight.

The molecular weight of the silk fibroin contained in each of the dialyzed aqueous silk fibroin solutions was measured by gel permeation chromatography. When the calcium chloride concentration was greater than 80% by weight as in Control Runs 2-(16) and 2-(17), the molecular weight was reduced to the order of 40,000. In the aqueous silk fibroin solutions prepared in accordance with this invention, however, the silk fibroin contained therein had a molecular weight of not less than 50,000 and showed no appreciable degree of hydrolysis.

These aqueous silk fibroin solutions were then adjusted, by either concentration or dilution, to the respective silk fibroin concentrations indicated in Table 2. Each of the resulting aqueous silk fibroin solutions was agitated at room temperature and at such a high speed as to give a shear rate of the order of 100/sec. In the course of 2–3 hours' agitation, the silk fibroin gradually precipitated and ultimately formed a mass of gel composed of a collection of small fragments of gel. However, when the silk fibroin concentration was less than 3% by weight as in Control Runs 2-(2) and 2-(9) or when it was greater than 20% by weight as in Control Runs 2-(8) and 2-(15), not a homogeneous mass of gel but a white precipitate was formed. This precipitate was too sticky to be separated by conventional filtration under reduced pressure. When it was placed in a cloth bag and then centrifuged, it aggregated into a bulky and sticky mass which was very difficult of dehydration and drying. In each run, the gel so formed was dehydrated by means of a centrifuge and then dried in hot air at 105° C. Using a jet mill, the resulting powder was pulverized and then subjected to a wet heat treatment comprising exposure to saturated steam at 120° C. for 15 minutes. The fine powder of silk fibroin consisted of nearly globular particles, 98% or more of which had diameters of 5–40μ.

When measurements of the bulk density were made, all the fine powders of silk fibroin produced in accordance with this invention were found to have values within the range of 0.1–0.7 g/cm³. The reason for this seems to be that the silk fibroin particles contained therein have minute pores owing to the special manner of production in which a powder is derived from a homogeneous mass of gel.

When measurements were made of the content of hot-water-insoluble fibron or rate of β-configuration, all the fine powders produced in accordance with this invention were found to have values of not less than 50% by weight. In addition, X-ray diffraction analysis revealed that the degree of crystallinity was not less than 25% in all the fine powders of silk fibroin produced in accordance with this invention.

TABLE 2

|  |  | Calcium Chloride Concentration (wt. %) | Solubility* | Silk Fibroin Concentration (wt. %) | Form of Gel | Rate of β-Configuration (%) | Average Molecular Weight (× 10⁴) | Bulk Density (g/cm³) |
|---|---|---|---|---|---|---|---|---|
| 2-(1) | Control Run | 3 | X | — | — | — | — | — |
| 2-(2) | " | 10 | O | 1 | Sticky precipitate | 28 | 10.2 | — |
| 2-(3) | Test Run | 10 | O | 10 | Soft mass | 72 | 10.2 | 0.48 |
| 2-(4) | " | 10 | O | 15 | " | 66 | 10.2 | 0.61 |
| 2-(5) | " | 20 | O | 5 | " | 83 | 9.8 | 0.40 |
| 2-(6) | " | 20 | O | 10 | " | 86 | 9.8 | 0.45 |
| 2-(7) | " | 20 | O | 20 | " | 80 | 9.8 | 0.47 |
| 2-(8) | Control Run | 20 | O | 25 | Sticky precipitate | 21 | 9.8 | 0.96 |
| 2-(9) | " | 40 | ⊚ | 1 | " | 42 | 8.6 | 0.74 |
| 2-(10) | Test Run | 40 | ⊚ | 10 | Soft mass | 98 | 8.6 | 0.33 |
| 2-(11) | " | 40 | ⊚ | 15 | " | 92 | 8.6 | 0.32 |
| 2-(12) | " | 40 | ⊚ | 20 | " | 90 | 8.6 | 0.32 |
| 2-(13) | " | 80 | ⊚ | 10 | " | 75 | 8.3 | 0.63 |
| 2-(14) | " | 80 | ⊚ | 20 | " | 77 | 8.3 | 0.70 |
| 2-(15) | Control Run | 80 | ⊚ | 25 | Sticky precipitate | 36 | 8.3 | 0.88 |
| 2-(16) | " | 90 | ⊚ | 10 | " | 48 | 4.2 | 0.93 |
| 2-(17) | " | 90 | ⊚ | 25 | " | 35 | 4.2 | 0.90 |

*Rated as insoluble (X) when the spun silk waste was not dissolved even after 24 hours, sparingly soluble (Δ) when it was dissolved in 1–2 hours, soluble (O) when it was dissolved in 0.5–1 hour, or very soluble (⊚) when it was dissolved within 0.5 hour.

EXAMPLE 3

Spun silk waste was degummed in the same manner as described in Example 1 and used as the starting material for the production of fine powders of silk fibroin. Anhydrous zinc chloride (ZnCl₂) was dissolved in water to prepare its aqueous solution having a zinc chloride concentration of 50% by weight, which was then heated to 70° C. According to the procedure of Example 2, spun silk waste was dissolved in the aqueous calcium chloride solution and the resulting solution was dialyzed and concentrated to prepare an aqueous silk fibroin solution having a silk fibroin concentration of 10% by weight. A 100-l portion of this aqueous silk fibroin solution was placed in a vessel and treated, with stirring, (1) by adding thereto 0.1 N sulfuric acid drop by drop until it was adjusted to pH 4.5 (isoelectric point) and then allowing it to stand at room temperature for 100 minutes, (2) by providing a 30 kHz ultrasonic wave generator on the inside wall of the vessel and operating it at room temperature for 1 hour, or (3) by using a pipe to feed air at a rate of 10 l/min. and bubble it through the aqueous silk fibroin solution for 10 minutes. In every case, the silk fibroin formed a mass of gel composed of a collection of small fragments of gel. This mass of gel was dehydraated by means of a centrifuge and then dried in hot air at 105° C. Using a jet mill, the resulting powder was pulverized to particle diameters of 5–40μ and, thereafter, subjected to a wet heat treatment comprising exposure to saturated steam at 120° C. for 30 minutes. The fine powder of silk fibroin thus obtained was tested for the content of hot-water-insoluble fibroin or rate of β-configuration (by estimation from the loss of weight on boiling in water), degree of crystallinity (by X-ray diffraction analysis), and bulk density. The results are given in Table 3.

Then, the three fine powders of silk fibroin produced according to the above-described procedure were evaluated with respect to several properties desired in base materials for cosmetic preparations. The results are given in Table 4. It can be seen from the data of this table that, when used in cosmetic preparations, all the fine powders of silk fibroin produced in Example 3 exhibited remarkably good properties.

TABLE 3

| | Content of Hot-water-insoluble Fibroin (wt.%) | Degree of Crystallinity (%) | Bulk Density (g/cm³) |
|---|---|---|---|
| Fine powder of silk fibroin produced by coagulation at the isoelectric point | 93 | 63 | 0.46 |
| Fine powder of silk fibroin produced by exposure to ultrasonic waves | 99 | 66 | 0.49 |
| Fine powder of silk fibroin produced by aeration | 86 | 47 | 0.57 |

TABLE 4

| | Moisture Absorption and Retention* | Affinity for the Skin* | Slip on the Skin* | Hydrophilic Lipophilic Balance* | Covering Power* |
|---|---|---|---|---|---|
| Fine powder of silk fibroin produced by coagulation at the iselectric point | ◉ | ○ | ○ | ◉ | ○ |
| Fine powder of silk fibroin produced by exposure to ultrasonic waves | ◉ | ◉ | ◉ | ○ | ◉ |
| Fine powder of silk fibroin produced by aeration | ◉ | ◉ | ○ | ○ | ○ |

*Rated as very good (◉), good (○), inadequate (Δ), or poor (X).

EXAMPLE 4

Spun silk waste was degummed in the same manner as described in Example 1 and used as the starting material for the production of fine powders of silk fibroin. An aqueous solution containing 8% by weight of ethylenediamine and 6% by weight of cupric hydroxide was prepared, and 10 parts of spun silk waste degummed as above was dissolved in 100 parts of the cupriethylenediamine solution by stirring at room temperature for 5 minutes. The resulting solution was immediately adjusted to pH 6.8 with 10% acetic acid and then diluted with water to prepare an aqueous silk fibroin solution having a silk fibroin concentration of 10% by weight. Then, according to the procedure of Example 2, this solution was dialyzed and concentrated to prepare an aqueous silk fibroin solution having a silk fibroin concentration of 15% by weight. The resulting aqueous silk fibroin solution was agitated at room temperature and at such a high speed as to give a shear rate of the order of 100/sec. In the course of 2–3 hours' agitation, the silk fibroin was gradually precipitated and ultimately formed a mass of gel. The mass of gel was dehydrated by means of a centrifuge and then dried in hot air at 105° C. Using a jet mill, the resulting powder was pulverized to particle diameters of 5–15μ and, thereafter, subjected to a wet heat treatment comprising exposure to saturated steam at 110° C. for 15 minutes. When the fine powder of silk fibroin thus obtained was tested, its content of hot-water-insoluble fibroin or rate of β-configuration was found to be about 83% by estimation from the loss of weight on boiling in water, and 80% by infrared spectroscopic analysis. Moreover, its degree of crystallinity was found to be about 56% by X-ray diffraction analysis and its bulk density was found to be 0.52 g/cm³. On the other hand, when a fine powder of silk fibroin produced in the same manner except for the omission of the wet heat treatment was tested, its content of hot-water-insoluble fibroin or rate of β-configuration was found to be 53% and its degree of crystallinity was found to be about 21%.

Then, the fine powders of silk fibroin produced according to the above-described procedure were evaluated with respect to several properties desired in base materials for cosmetic preparations. The results are given in Table 5. It can be seen from the data of this table that, when used in cosmetic preparations, the fine powders of silk fibroin produced in accordance with this invention exhibited remarkably good properties.

TABLE 5

| | Moisture Absorption and Retention* | Affinity for the Skin* | Slip on the Skin* | Hydrophilic-Lipophilic Balance* | Covering Power* |
|---|---|---|---|---|---|
| Fine powder of silk fibroin subjected to a wet heat treatment | ◉ | ◉ | ◉ | ○ | ○ |
| Fine powder of silk fibroin subjected to no wet heat treatment | ◉ | ○ | ○ | ○ | ○ |

*Rated as very good (◉), good (○), inadequate (Δ), or poor (X).

Furthermore, the fine powder of silk fibroin produced in accordance with this invention and then subjected to a wet heat treatment, a conventional powder of silk fibroin in fibrous form, and a powder of silk fibroin having a rate of β-configuration of 10% or less (as produced by spray-drying a colloidal solution of silk fibroin) were evaluated with respect to several properties desired in base materials for cosmetic preparations.

The results are given in Table 6. It can be seen from the data of this table that, when used in cosmetic preparations, the fine powder of silk fibroin produced in accordance with this invention exhibited remarkably good properties.

TABLE 6

| | Moisture Absorption and Retention* | Affinity for the Skin* | Slip on the Skin* | Hydrophilic-Lipophilic Balance* | Covering Power* |
|---|---|---|---|---|---|
| Fine powder of silk fibroin in accordance with this invention | ⊙ | ⊙ | ⊙ | ○ | ○ |
| Powder of silk fibroin in fibrous form | Δ | Δ | Δ | ○ | X |
| Powder of silk fibroin having a rate of β-configuration of 10% or less | ⊙ | X | X | X | X |

*Rated as very good (⊙), good (○), inadequate (Δ), or poor (X).

EXAMPLE 5

A series of fine powders of silk fibroin were produced in the same manner as described in Example 2. In this example, however, aqueous silk fibroin solutions having silk fibroin concentrations of 3.3–8.5% by weight were prepared according to the respective methods indicated in Table 7 and the silk fibroin was precipitated from these solutions according to the respective methods also indicated in Table 7. The resulting masses of gel were dehydrated and dried, subjected to a wet heat treatment at 110° C. for 30 minutes, and then pulverized to particle diameters of 1–50μ by means of a jet mill. Though slight variations were noted according to the methods of dissolution and precipitation, the fine powders of silk fibroin thus obtained had contents of hot-water-insoluble fibroin ranging from 70 to 95% by weight and degrees of crystallinity ranging from 40 to 60%.

It can be seen from the data of Table 7 that, when used as a base material for cosmetic preparations, the fine powders of silk fibroin produced according to the various methods of dissolution exhibited remarkably good properties.

TABLE 7

| Method of Dissolution | Method of Precipitation | Moisture Absorption and Retention* | Affinity for the Skin* | Slip on the Skin* | Hydrophilic Lipophilic Balance* | Covering Power* |
|---|---|---|---|---|---|---|
| Dissolved in Schweitzer's reagent [see JIS P8101 (57)] at room temperature | Precipitated by the addition of sodium chloride to a concentration of 5% | ⊙ | ○ | ○ | ○ | ○ |
| Dissolved in 70% lithium bromide at 60° C. | Precipitated by agitation at a shear rate of 200/sec. | ⊙ | ○ | ⊙ | ○ | ○ |
| Dissolved in 40% calcium nitrate at 85° C. | Precipitated by agitation at a shear rate of 200/sec. | ⊙ | ⊙ | ⊙ | ⊙ | ○ |
| Dissolved in 60% magnesium nitrate at 100° C. | Precipitated by agitation at a shear rate of 200/sec. | ⊙ | ⊙ | ⊙ | ○ | ○ |
| Dissolved in 20% calcium thiocyanate at 60° C. | Precipitated by the addition of sodium chloride to a concentration of 5% | ⊙ | ○ | ○ | | |
| Dissolved in 50% sodium thiocyanate at 60° C. | Precipitated by the addition of sodium sulfate to a concentration of 5% | ○ | ⊙ | ○ | ○ | |
| Dissolved in 40% magnesium thiocyanate at 60° C. | Precipitated by the addition of sodium sulfate to a concentration of 5% | ⊙ | ○ | ○ | ○ | ○ |
| Dissolved in 45% magnesium chloride at 60° C. | Precipitated by agitation at a shear rate of 50/sec. | ⊙ | ⊙ | ○ | ○ | ○ |

*Rated as very good (⊙), good (○), inadequate (Δ), or poor (X).

What is claimed is:

1. A process for producing a fine powder of silk fibroin in nonfibrous and particulate form which has an average molecular weight of not less than 50,000, a degree of molecular orientation equal to not greater than one-half that of natural silk thread, particle diameters of from 1 to 100μ, and a bulk density of from 0.1 to 0.7 g/cm³ as measured in the dry state and which contains at least 50% by weight of hot-water-insoluble fibroin having the β-configuration, the process comprising the steps of dissolving a degummed silk material in at least one solvent selected from the group consisting of an aqueous cupri-ethylenediamine solution, an aqueous ammoniacal solution of cupric hydroxide, an aqueous alkaline solution of cupric hydroxide and glycerol, an aqueous lithium bromide solution, an aqueous solution of the chloride, nitrate or thiocyanate of calcium, magnesium or zinc, and an aqueous sodium thiocyanate solution; adding a coagulating salt to the resulting aqueous silk fibroin solution having a silk fibroin concentration of from 3 to 20% by weight to coagulate and precipitate the silk fibroin; dehydrating and drying the gel so formed; and then pulverizing the resulting powder.

2. A process for producing a fine powder of silk fibroin in nonfibrous and particulate form which has an average molecular weight of not less than 50,000, a degree of molecular orientation equal to not greater than one-half that of natural silk thread, particle diameters of from 1 to 100μ, and a bulk density of from 0.1 to 0.7 g/cm$^3$ as measured in the dry state and which contains at least 50% by weight of hot-water-insoluble fibroin having the β-configuration, the process comprising the steps of dissolving a degummed silk material in at least one solvent selected from the group consisting of an aqueous cupri-ethylenediamine solution, an aqueous ammoniacal solution of cupric hydroxide, an aqueous alkaline solution of cupric hydroxide and glycerol, an aqueous lithium bromide solution, an aqueous solution of the chloride, nitrate or thiocyanate of calcium, magnesium or zinc, and an aqueous sodium thiocyanate solution; dialyzing the resulting aqueous silk fibroin solution; subjecting the dialyzed aqueous silk fibroin solution having a silk fibroin concentration of from 3 to 20% by weight to at least one treatment for coagulating and precipitating the silk fibroin, the treatment being selected from the group consisting of the addition of a coagulating salt, aeration, coagulation at the isoelectric point, exposure to ultrasonic waves, and agitation at high shear rate; dehydrating and drying the gel so formed; and then pulverizing the resulting powder.

3. A process as claimed in claim 1 or 2 wherein the solvent is an aqueous solution of the chloride or nitrate of calcium or magnesium.

4. A process as claimed in claim 1 or 2 wherein the coagulating salt is ammonium sulfate, sodium sulfate, or sodium chloride.

5. A process as claimed in claim 2 wherein the aeration is carried out by bubbling air through the aqueous silk fibroin solution for a period of 1 hour or more, the air being fed at a rate of at least 0.1 l/min. for each liter of the aqueous silk fibroin solution.

6. A process as claimed in claim 2 wherein the coagulation at the isoelectric point is carried out by adjusting the aqueous silk fibroin solution to pH 4.5 and then allowing it to stand at room temperature for a period of 10 minutes or more.

7. A process as claimed in claim 2 wherein the exposure to ultrasonic waves is carried out by generating ultrasonic waves having frequencies of 30 kHz or higher and exposing the aqueous silk fibroin solution to these ultrasonic waves for a period of 1 hour or more.

8. A process as claimed in claim 2 wherein the agitation is carried out at a shear rate of 50/sec or more.

9. A process as claimed in claim 1 or 2 wherein the powder resulting from the dehydration and drying step is subjected to a wet heat treatment comprising exposure to saturated steam at a temperature of 50° C. or above.

10. A process as claimed in claim 1 or 2 wherein, prior to drying, the dehydrated gel is heat-treated in an aqueous ammonium sulfate solution at a temperature of 50° C. or above.

11. A process as claimed in claim 2 wherein the dialysis step is carried out by the use of a multilayer membrane structure or bundled hollow-fiber structure satisfying the condition expressed by $$\frac{\text{Membrane Surface Area (cm}^2\text{)}}{\text{Priming Volume (cm}^3\text{)}} \geq 100$$

* * * * *